US009423381B2

(12) United States Patent
Jaramillo et al.

(10) Patent No.: US 9,423,381 B2
(45) Date of Patent: Aug. 23, 2016

(54) SELF-PROPELLED, REDUCED-WATER, INTERNAL NON-DESTRUCTIVE INSPECTION APPARATUS

(71) Applicant: Spirit AeroSystems, Inc., Wichita, KS (US)

(72) Inventors: Todd Brian Jaramillo, Wichita, KS (US); Kendall Ford Koerner, Wellington, KS (US); Allison Jean Wright, Wichita, KS (US)

(73) Assignee: Spirit AeroSystems, Inc., Wichita, KS (US)

( * ) Notice: Subject to any disclaimer, the term of this patent is extended or adjusted under 35 U.S.C. 154(b) by 604 days.

(21) Appl. No.: 13/803,706

(22) Filed: Mar. 14, 2013

(65) Prior Publication Data

US 2014/0260629 A1    Sep. 18, 2014

(51) Int. Cl.
  *G01N 29/265*    (2006.01)
  *G01N 29/22*    (2006.01)
  *G01N 29/04*    (2006.01)
  *G01N 29/28*    (2006.01)
  *G01N 29/44*    (2006.01)

(52) U.S. Cl.
  CPC .......... *G01N 29/265* (2013.01); *G01N 29/041* (2013.01); *G01N 29/221* (2013.01); *G01N 29/225* (2013.01); *G01N 29/28* (2013.01); *G01N 29/4436* (2013.01); *G01N 2291/0231* (2013.01)

(58) Field of Classification Search
  CPC ............. G01N 29/221; G01N 29/225; G01N 29/265; G01N 29/28
  See application file for complete search history.

(56) References Cited

U.S. PATENT DOCUMENTS

| 6,138,515 A * | 10/2000 | Moufle et al. ................... 73/639 |
| 2005/0215901 A1* | 9/2005 | Anderson ................ A61B 8/12 600/445 |
| 2008/0066553 A1* | 3/2008 | Espada Tejedor .............. 73/627 |
| 2012/0060609 A1* | 3/2012 | Fukutomi et al. .............. 73/592 |

FOREIGN PATENT DOCUMENTS

WO    WO 2004062460 A2 *    7/2004

\* cited by examiner

*Primary Examiner* — Paul West
(74) *Attorney, Agent, or Firm* — Hovey Williams LLP

(57) ABSTRACT

An inspection apparatus and method for inspecting an inner surface of a hollow composite part. The inspection apparatus may have a support frame, at least one transducer attached to the support frame, an ultrasound gel pad attached to an outer surface of the transducer, and a sponge attached to the support frame. The transducer may send and receive ultrasound waves and the sponge may be positioned to leave a trail of water when moved along the inner surface of the hollow composite part, such that the water rests between the ultrasound gel pad and the inner surface once the inspection apparatus reaches a location to be inspected. The ultrasound waves may thus be transmitted through the ultrasound gel pad and then through the water before bouncing off of the inner surface of the hollow composite part. The ultrasound waves bounced off of the inner surface may be detected by the transducer and analyzed to determine if there is a defect in the composite part.

17 Claims, 8 Drawing Sheets

SELF-PROPELLED, REDUCED-WATER, INTERNAL NON-DESTRUCTIVE INSPECTION APPARATUS

BACKGROUND

Composite materials are increasingly replacing metals in aerospace structural applications due to their high strength and low weight. Composite materials may also be co-cured into large, complex, integrated structures, potentially reducing weight, manufacturing costs, and fastener counts. However, these complex integrated structures are often difficult to adequately inspect because critical inspection locations are closed-in and inaccessible to existing non-destructive inspection (NDI) equipment available in the industry.

The above-described problem commonly occurs when hollow "hat"-type stringers run through the interior of a structure and are therefore not accessible for inspection by conventional means. Inspecting aircraft stringer-rib bond lines is particularly difficult using known methods.

One known method for inspecting tubular structures, such as water pipelines, includes the use of pipeline inspection "pigs" configured to inspect inaccessible tubular structures from the inside. These pigs operate in a liquid-filled environment and are moved via fluid flowing within a pipeline with no independent means of positioning. These pigs are designed to operate in completely filled pipelines and do not provide a way of limiting immersion fluids to a specific area under inspection. Specifically, it may be desirable to avoid any water entering components near to the inspection area in some applications.

Accordingly, there is a need for an improved method of inspecting composite parts that overcomes the limitations of the prior art.

SUMMARY

This summary is provided to introduce a selection of concepts in a simplified form that are further described below in the detailed description. This summary is not intended to identify key features or essential features of the claimed subject matter, nor is it intended to be used to limit the scope of the claimed subject matter. Other aspects and advantages of the present invention will be apparent from the following detailed description of the preferred embodiments and the accompanying drawing figures.

Embodiments of the present invention solve the above-mentioned problems and provide a distinct advance in the art of composite part inspection. An inspection apparatus constructed in accordance with embodiments of the invention for inspecting a composite part may include a support frame, an inspection probe attached to the support frame, a conforming solid material attached to an outer surface of the inspection probe, and a pre-wetting apparatus attached to the support frame. The inspection probe may send and receive wireless signals, such as ultrasound waves, for inspecting an inner surface of a composite part. The conforming solid material may propagate the wireless signals from the inspection probe therethrough. The pre-wetting apparatus may be positioned to leave a trail of liquid on a surface to be inspected by the inspection probe prior to the inspection probe reaching the surface. The inspection probe may be or include a transducer, the conforming solid material may be an ultrasound gel pad, and the pre-wetting apparatus may be a weeping sponge or similar apparatus.

Another embodiment of the invention is a method for inspecting an inner surface of a hollow composite part. The method may include the steps of actuating the inspection apparatus through at least a portion of the hollow composite part until the inspection apparatus rests at a location to be inspected. Because of the position of the pre-wetting apparatus, this actuation allows the pre-wetting apparatus or sponge to slide along the inner surface of the composite part ahead of the transducer, so that a thin layer of water may be present between the ultrasound gel pad and the inner surface. Next, the method may include sending ultrasound waves from the transducer through the ultrasound gel pad and the water on the inner surface of the hollow composite part. Then the method may include receiving, with the transducer, ultrasound waves reflected off of an exterior and/or interior of the hollow composite part to determine if any defects are present within the composite part.

BRIEF DESCRIPTION OF THE DRAWING FIGURES

Embodiments of the present invention are described in detail below with reference to the attached drawing figures, wherein.

Figure 1:
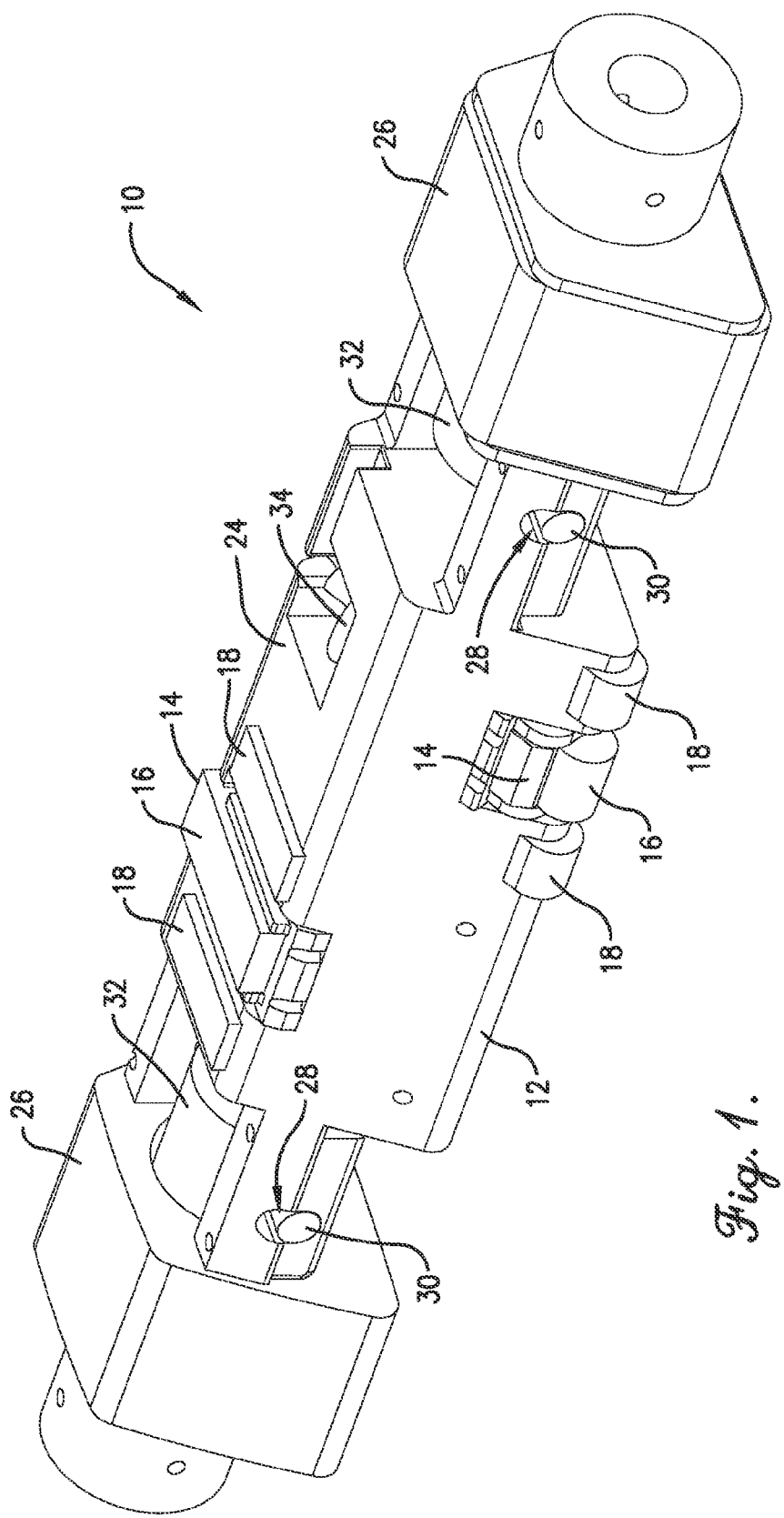
FIG. 1 is a perspective view of an inspection apparatus constructed in accordance with an embodiment of the invention.

The drawing figures do not limit the present invention to the specific embodiments disclosed and described herein. The drawings are not necessarily to scale, emphasis instead being placed upon clearly illustrating the principles of the invention.

DETAILED DESCRIPTION

The following detailed description of the invention references the accompanying drawings that illustrate specific embodiments in which the invention can be practiced. The embodiments are intended to describe aspects of the invention in sufficient detail to enable those skilled in the art to practice the invention. Other embodiments can be utilized and changes can be made without departing from the scope of the present invention. The following detailed description is, therefore, not to be taken in a limiting sense. The scope of the present invention is defined only by the appended claims, along with the full scope of equivalents to which such claims are entitled.

In this description, references to "one embodiment", "an embodiment", or "embodiments" mean that the feature or features being referred to are included in at least one embodiment of the technology. Separate references to "one embodiment", "an embodiment", or "embodiments" in this description do not necessarily refer to the same embodiment and are also not mutually exclusive unless so stated and/or except as will be readily apparent to those skilled in the art from the description. For example, a feature, structure, act, etc. described in one embodiment may also be included in other embodiments, but is not necessarily included. Thus, the present technology can include a variety of combinations and/or integrations of the embodiments described herein.

An inspection apparatus 10 constructed in accordance with embodiments of the present invention is shown in FIGS. 1-7 and generally includes a support frame 12, inspection probes 14 supported by the support frame 12, a conforming solid material 16 attached to an outer surface of the inspection probes 14, and at least one pre-wetting apparatus 18. The inspection apparatus 10 may be configured for non-destructive inspection (NDI) a hollow composite part 20, such as the composite stringer illustrated in FIG. 3, and specifically may inspect an inner surface 22 of the hollow composite part 20. The inspection apparatus 10 may be movable within the hollow composite part 20 to enable short sections of the hollow composite part 20, such as a stringer, to be inspected without water entering undesired sections of the composite part 20.

The support frame 12 may be an elongated structure comprising a central trolley portion 24 and centering devices 26 or plugs at opposing ends thereof. The central trolley portion 24 may support the inspection probes 14, conforming solid material 16, and/or the pre-wetting apparatus 18 between the centering devices 26. Alternatively, one or more of the centering devices 26 may support the pre-wetting apparatus 18.

The centering devices 26 may be sized and shaped to fit within a cavity or hollow tube portion of the composite part 20 and substantially conform to a cross-sectional shape or inner surface 22 of the composite part 20, such as the stringer, thereby centering the central trolley portion 24 and the inspection probes 14 relative to the hollow composite part 20. For example, the centering devices 26 may have a substantially trapezoidal shape and may be configured to fit into a hollow composite stringer or a hat-type composite stringer bonded to another composite part to form a hollow tube having a substantially trapezoid-shaped cross-section. However, note that embodiments of the invention may be configured to inspect hollow parts of any material or combination of materials and of any shape and size without departing from the scope of the invention. The centering devices 26 may be made of a substantially solid material or a somewhat malleable material such as a rubber or foam which may be compressed in situations where there is at least a small amount of variation in the cross-section of the composite part 20 being inspected.

Figure 6:
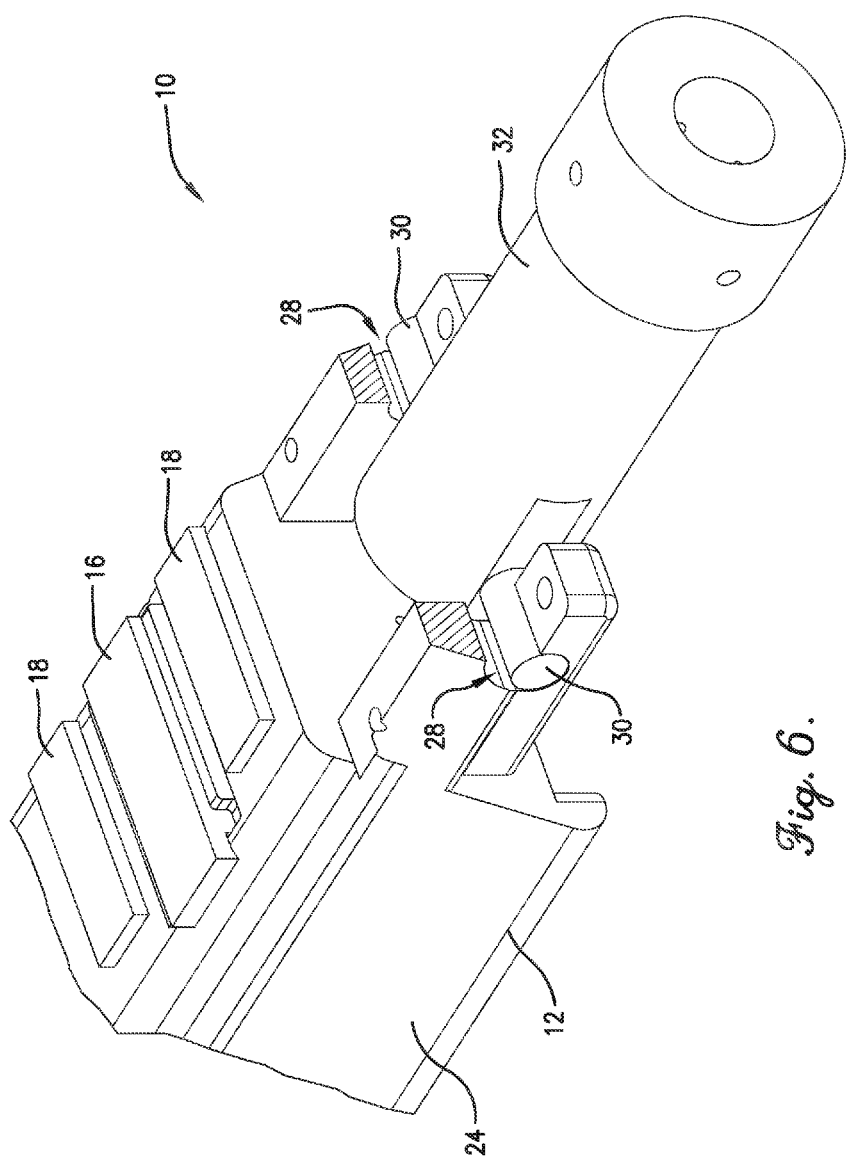
FIG. 6 is a cut-away perspective view of a pivot point of a support frame of the inspection apparatus of FIG. 1.

Various portions of the support frame 12 may be configured to articulate, flex, or pivot at one or more points to accommodate for non-linear paths of travel within the composite part 20. For example, if a hollow stringer is not fully linear throughout, but rather has a section that is angled, slanted, or sloped in comparison to another linear portion thereof, a portion of the support frame 12 may pivot or flex about one or more pivot points to fit therethrough. Specifically, as illustrated in FIGS. 1 and 6, slotted or elongated holes 28 with cylindrical pins 30 resting therein may link the centering devices 26 with the central trolley portion 24 such that the centering devices 26 may be pivoted relative to the central trolley portion 24. For example, the cylindrical pins 30 may protrude from either side of an extension arm 32 extending from one of the centering devices 26 toward the central trolley portion 24.

Figure 2:
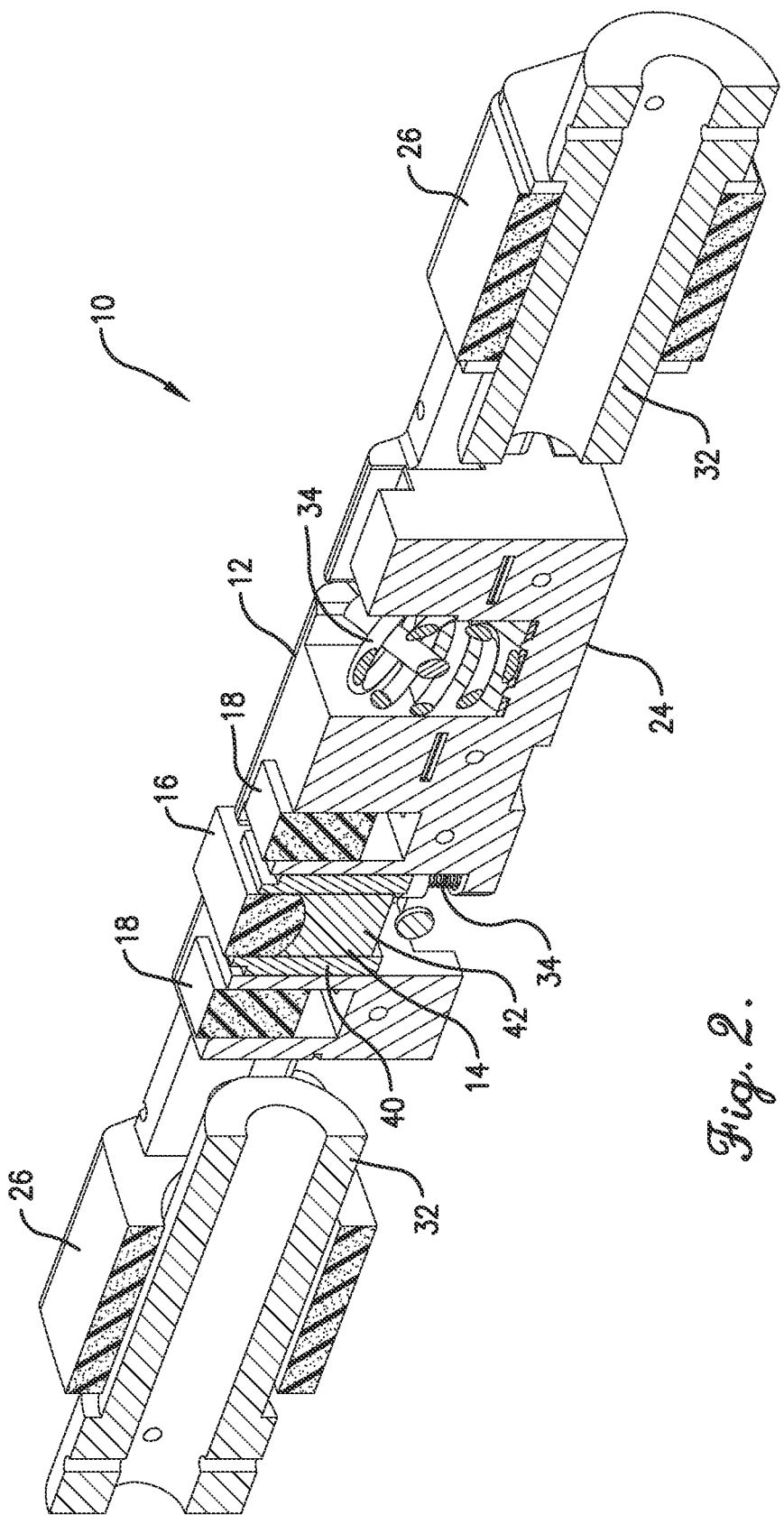
FIG. 2 is a cross-sectional perspective view of the inspection apparatus of FIG. 1.
Figure 3:
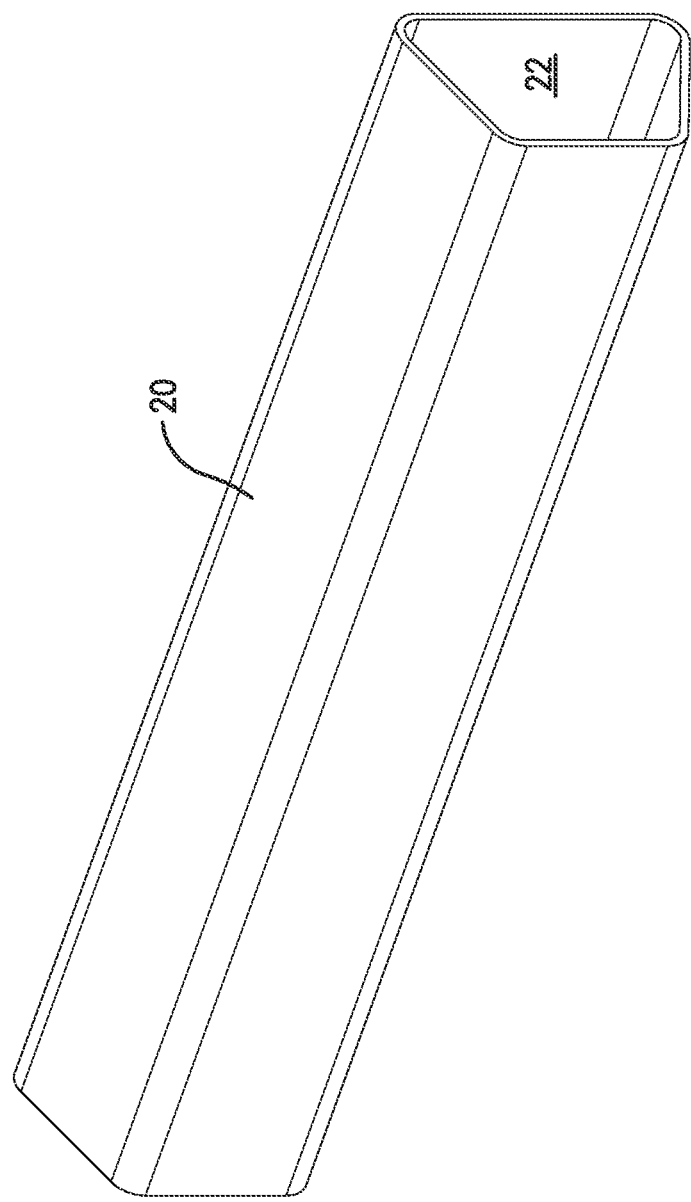
FIG. 3 is a perspective view of a hollow composite part to be inspected by the inspection apparatus of FIG. 1.

As illustrated in FIG. 2, the support frame 12 may further comprise a spring 34 or other resilient member connecting the central trolley portion 24 with the inspection probes 14. The spring 34 or springs provide an expandable design configured to maintain the inspection probes 14 at a desired alignment, despite variations in cross-section of the composite part 20.

Figure 7:
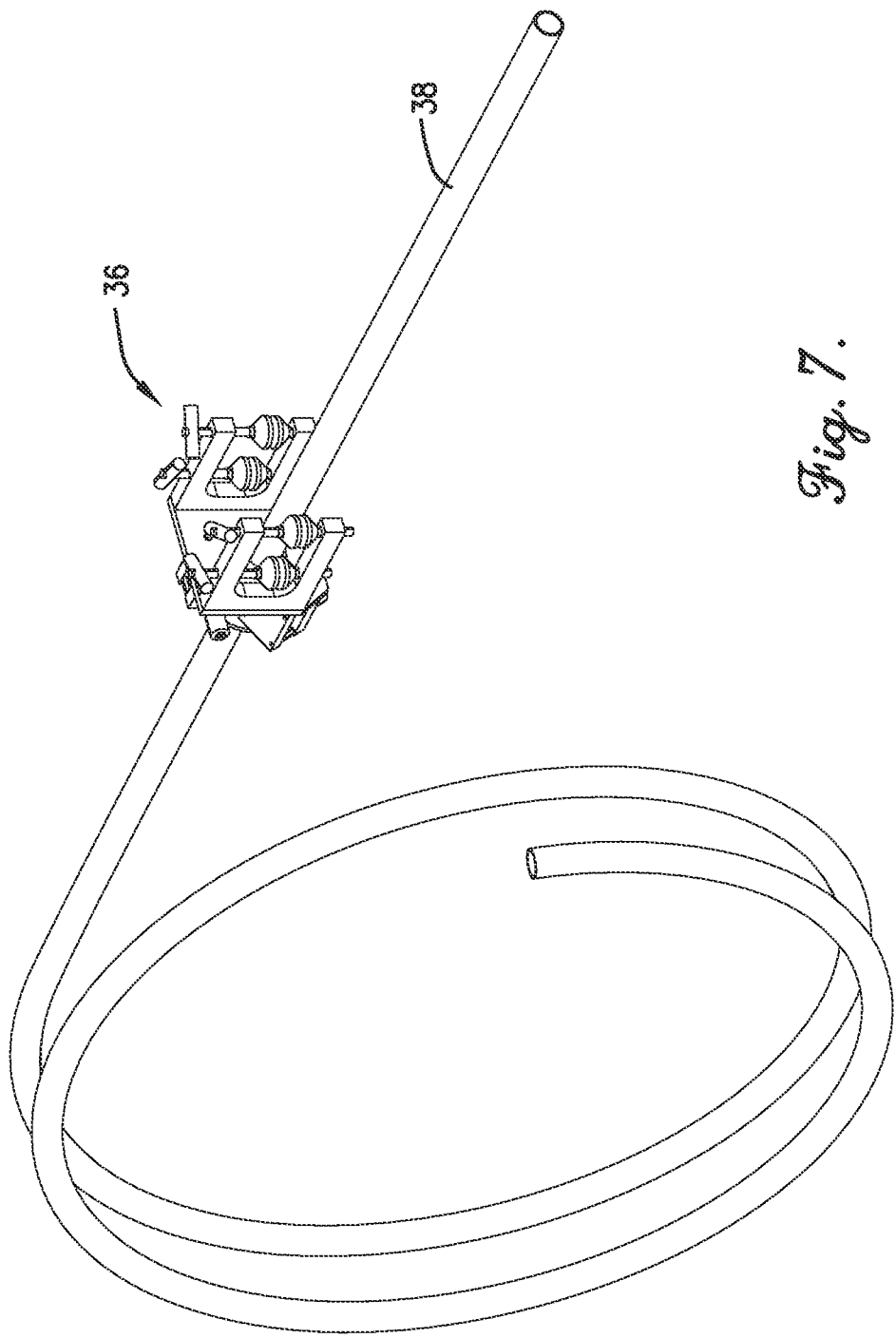
FIG. 7 is a perspective view of a motor system constructed in accordance with an embodiment of the invention to actuate the inspection apparatus of FIG. 1.

The support frame 12 may be positioned within the hollow composite part 20 using any actuation means. For example, a motor system 36, as illustrated in FIG. 7, having one or more DC motors could be used to propel the support frame through the composite part 20. Furthermore, a winch-like system for pulling cable driven embodiments of the invention may be used, or friction drive rollers may be used for pushing and pulling an elongated actuation element 38 attached to the support frame 12. Alternatively, various electrical, mechanical, hydraulic, and/or manual actuation systems could be employed to slide the support frame 12 and inspection probes 14 along the inner surface 22 of the composite part 20 as inspection data is being gathered by the inspection probes 14.

In some embodiments of the invention, the inspection apparatus 10 may further comprise an encoder (not shown) configured to provide positional information, such as the position of the inspection apparatus 10 within the composite part, to a non-destructive inspection (NDI) system. For example, the encoder may be mounted externally to the composite part 20 and may sense movement of the inspection apparatus 10. Alternatively, the encoder may be positioned between the centering devices 26 to directly sense motion of the support frame 12. The encoder may be, for example, a magnetic encoder comprising a permanent magnet tape used in conjunction with a Hall Effect sensor chip.

Figure 4:
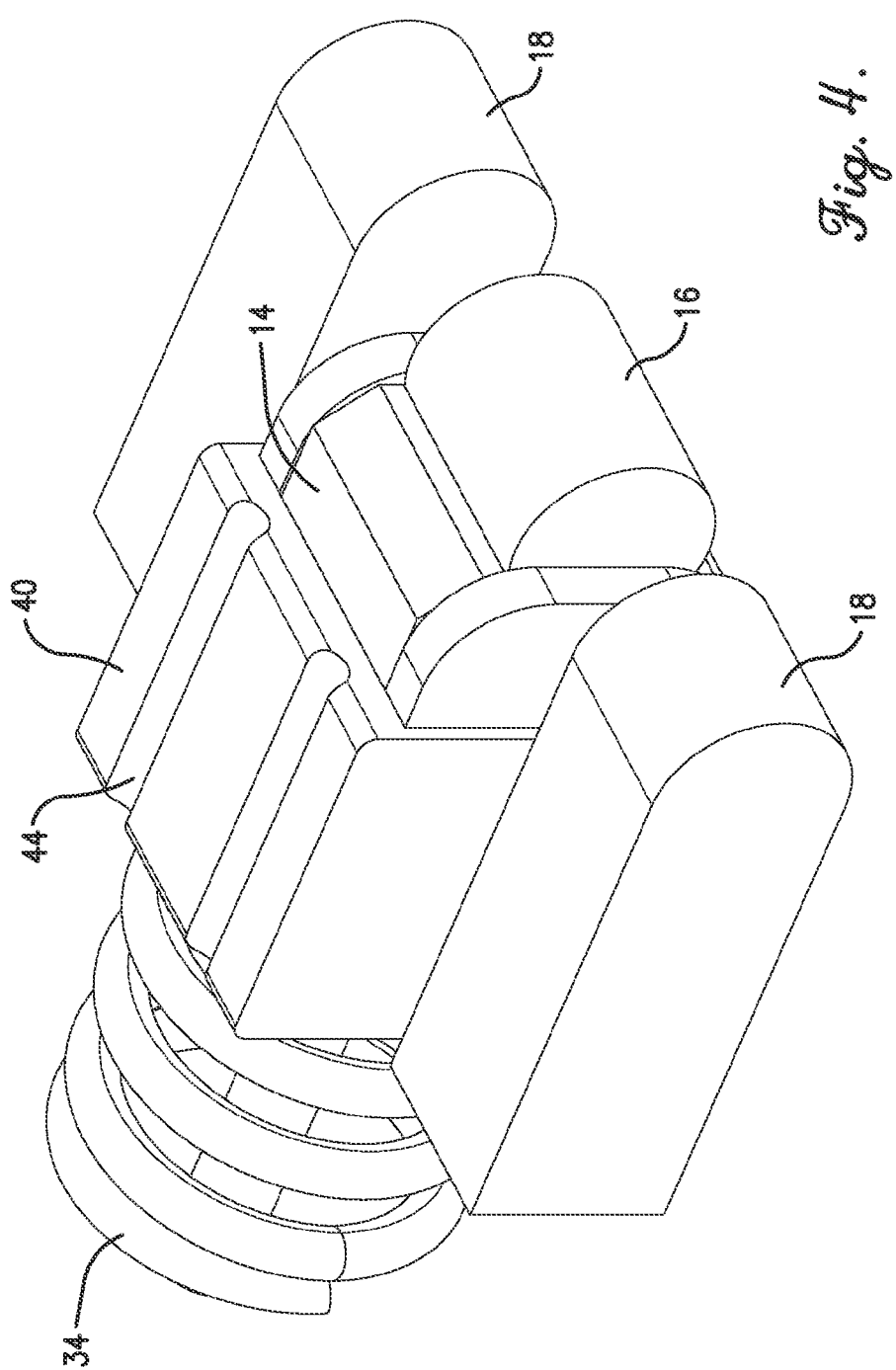
FIG. 4 is a first inspection probe of the inspection apparatus of FIG. 1.
Figure 5:
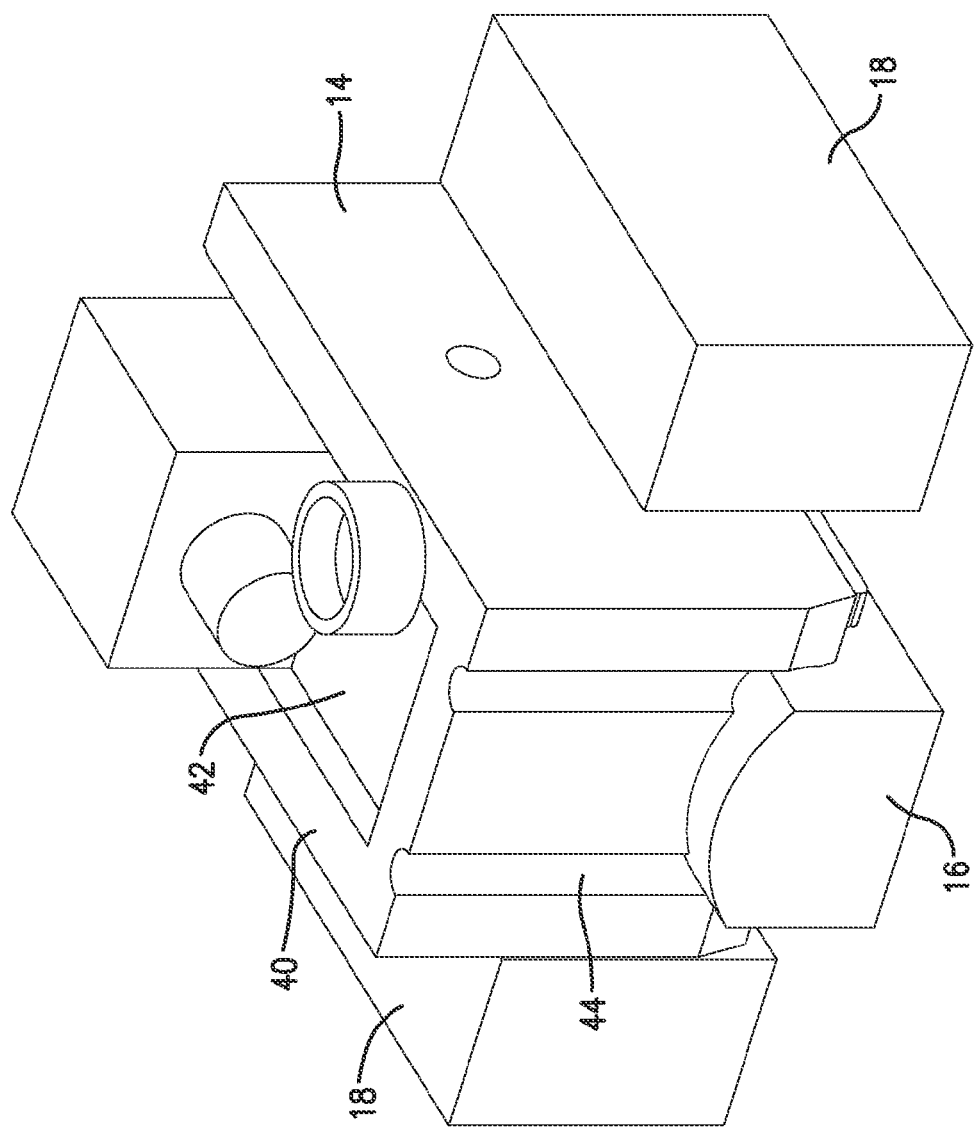
FIG. 5 is a second inspection probe of the inspection apparatus of FIG. 1.

As illustrated in FIGS. 2, 4, and 5, the inspection probes 14 may comprise a housing 40 and one or more transducers 42, an array of transducers, or any other sensor configured to send and receive wireless signals such as light or sound waves. Note that light waves may include light waves outside of the visible spectrum and sound waves may include sound waves beyond the limits of the audible spectrum. For example, the inspection probes 14 may include transducers that output ultrasonic waves and receive ultrasonic waves bouncing off of a surface such as the inner surface 22 of the composite part 20 noted above for inspection.

The housing 40 may engage with the spring 34 or resilient member, as illustrated in FIG. 2. Furthermore, as illustrated in FIGS. 4 and 5, the housing 40 may also comprise various channels 44 formed therein and configured to interface with portions of the support frame 12 to properly maintain linear motion relative to a center axis of the spring 34. In some embodiments of the invention, the conforming solid material 16 may be attached directly to the housing 40.

The conforming solid material 16 may provide ultrasonic coupling between the inspection probe 14 or transducers and the surface of the composite part 20 being inspected. The conforming solid material 16 may be fixed to an outer surface of the inspection probes 14 or transducers 42 such that waves sent from the transducers 42 are propagated through the conforming solid material 16 to the composite part 20. The conforming solid material 16 may be a solid or gel couplant sufficient to adequately propagate ultrasonic waves sent and received therethrough. For example, the conforming solid material 16 may be an ultrasound gel pad such as AQUAFLEX® ultrasound gel or gel pads manufactured by Parker Laboratories of Fairfield, N.J., rubber, thermoplastic elastomer (TPE), styrene block copolymer, or any other conforming solid material that propagates sound and has a relative low attenuation of ultrasonic waves. The ultrasound gel pads may be aqueous, flexible ultrasound standoffs for use in difficult to visualize and near field areas, such as those traditionally used in medical diagnostic and therapeutic ultrasound procedures.

The conforming solid material 16 may be manufactured to have any size or shape as desired for a given inspection application. For example, as illustrated in FIGS. 1, 2, and 5, the conforming solid material 16 may have a substantially flat surface configured to interface with a substantially planar surface. Additionally or alternatively, as illustrated in FIGS. 1, 2, and 4, the conforming solid material 16 may have a radiused surface configured to interface with an angled or radiused surface or multiple angled surfaces of the composite part 20.

The pre-wetting apparatus 18 may be, for example, high volume sponges, weeping sponges, spray nozzles, or any other device or apparatus for applying a small amount (or "snail trail") of liquid or water to a surface. The pre-wetting apparatus 18 may be fed with water internally with a liquid delivery component such as pipes or spray nozzles to create the "snail trail" pre-wet effect along the path traveled by the pre-wetting apparatus 18 and the associated inspection probe 14 on the inner surface 22 of the composite part 20. Alternatively, the pre-wetting apparatus 18 may be saturated with water prior to insertion into the composite part 20. The pre-wetting apparatus 18 or sponge may keep the conforming solid material 16 substantially coupled to the inner surface 22 of the composite part 20. The amount of liquid or water provided by the pre-wetting apparatus 18 may be a minimum amount required for acoustic coupling.

The pre-wetting apparatus 18 may be fixed at opposing ends of each of the inspection probes 14, such that the inspection probe 14 is located between two pre-wetting apparatuses 18. By having pre-wetting apparatuses 18 on either side of the inspection probes, the inspection apparatus 10 can be moved forward or backward within the composite part 20 and still provide pre-wetting to the inner surface 22 of the composite part 20. Alternatively, a single pre-wetting apparatus 18 may be positioned ahead of the inspection probe 14 such that it slides over the inner surface 22 of the composite part 20 prior to the inspection probe 14 reaching the locations therein to be inspected.

The pre-wetting apparatuses 18 coat the inner surface 22 of the composite part 20 with liquid or water to acoustically couple the conforming solid material 16 to the composite part 20. However, the pre-wetting apparatuses 18 do not need to fill any portion of the composite part 20 with water, because the ultrasound waves from the transducer 42 are propagated through the conforming solid material 16. The trail or coating of water applied by the pre-wetting apparatuses 18 merely serve to compensate for any small inconsistencies in the inner surface 22 of the composite part 20, where the conforming solid material 16 may not provide an intimate enough contact with the inner surface 22.

In use, the inspection apparatus 10 may be positioned within the composite part 20, such as within a stringer, or a hat-type stringer bonded to another composite skin. The inspection apparatus 10 may then be pushed or pulled by any actuation means, such as the motor system 36 described above, to properly position the inspection apparatus 10 within the composite part 20. For example, the composite part 20 may have some holes or cavities intentionally formed therein in which water or fluid should not enter. Therefore, the inspection apparatus 10 may be properly positioned via user knowledge of the areas to be tested and/or using information from the encoder to ensure that the inspection apparatus 10 is properly positioned within the composite part 20.

Then fluid, such as water, may saturate the pre-wetting apparatus 18 or weeping sponges by either feeding a small continuous amount of fluid to the pre-wetting apparatus 18 via tubing or other fluid delivery means or by an initial saturation of the pre-wetting apparatus 18. Any method of providing a small amount of fluid to a surface of the area to be inspected, ahead of the inspection probes 14, may be used without departing from the scope of the invention. Then the inspection probes 14 may take desired readings within the composite part 20, as described above. Specifically, the inspection probes 14 may output sound (e.g., ultrasound waves) and/or light waves or the like and may then receive reflections resulting from these waves bouncing off of an exterior or interior surface of the composite part 20 or a defect within the thickness of the composite part 20. For example, the waves may bounce off of the inner surface 22 of the composite part 20 or may pass through the inner surface 22 and bounce off of a back surface of the composite part or off of any defects present through the thickness of the composite part within the area being inspected. Specifically, the inspection probes 14 may send ultrasonic waves through the conforming solid material 16 and then through the liquid or water deposited on the inner surface 22 of the composite part 20 by the pre-wetting apparatus 18. Ultrasound waves that travel through the inner surface 22 may be reflected from either a back-wall or outermost surface of the composite part 20, or may be reflected by some defect present in the middle or thickness of the composite part 20. This allows detection of potential hidden defects within the thickness of the composite part 20 which can not be visually seen on the inner surface 22 or an outer surface of the composite part 20.

The resilient members or springs 34 connecting the inspection probes 14 with the support frame 12 may naturally compress or release to their naturally-biased configuration depending on the cross-sectional size and shape of the composite part 20, thus providing substantially intimate contact between the conforming solid material 16 and the inner surface 22 of the composite part 20, with just a thin layer of water between the conforming solid material 16 and the inner surface 22.

Figure 8:
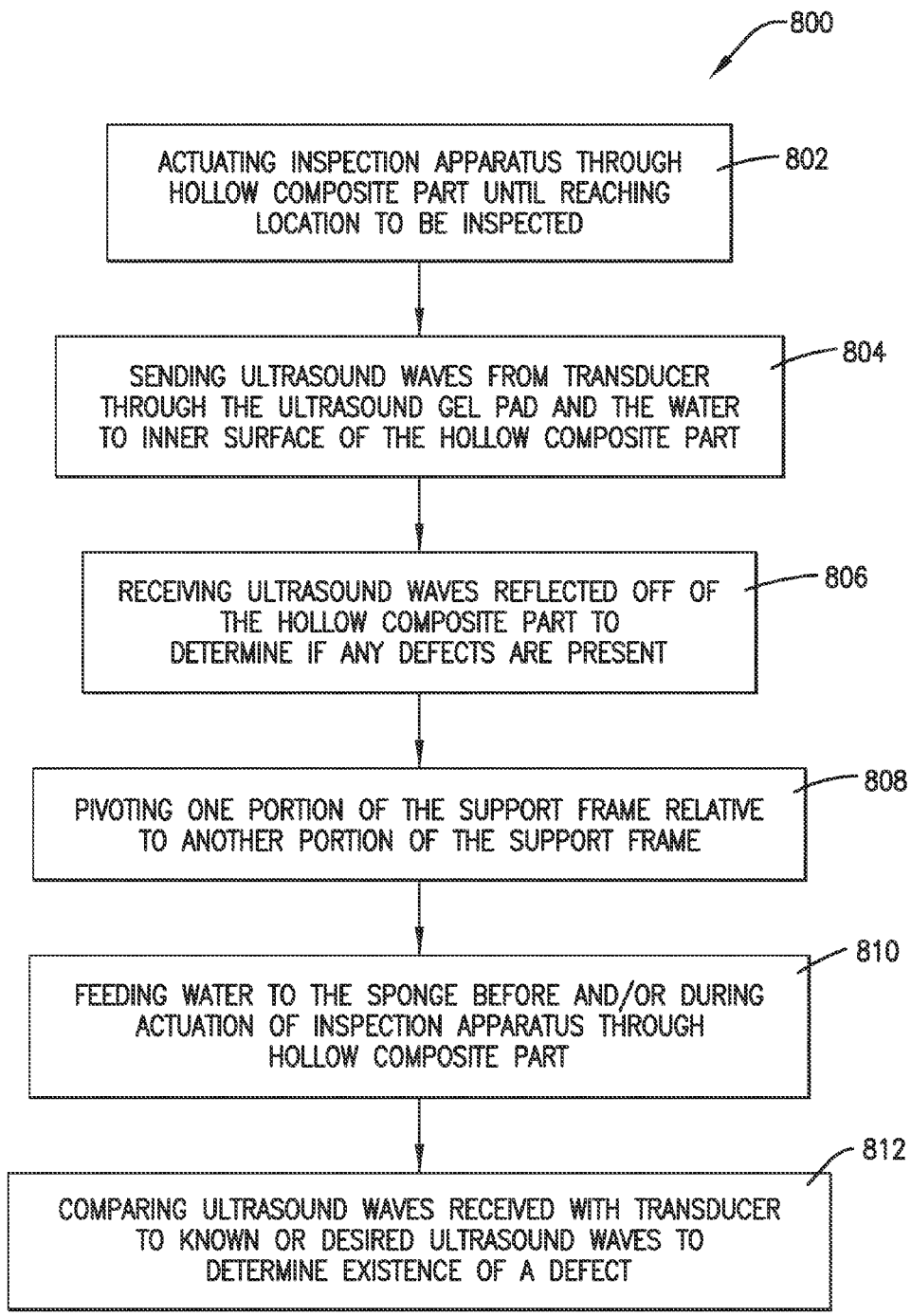
FIG. 8 is a flow chart of a method of inspecting a composite part in accordance with an embodiment of the invention.

The flow chart of FIG. 8 depicts the steps of an exemplary method 800 for inspecting a hollow composite part. In some alternative implementations, the functions noted in the various blocks may occur out of the order depicted in FIG. 8. For example, two blocks shown in succession in FIG. 8 may in fact be executed substantially concurrently, or the blocks may sometimes be executed in the reverse order depending upon the functionality involved.

The method 800 may comprise the steps of actuating the inspection apparatus 10 through at least a portion of the hollow composite part 20 until the inspection apparatus 10 rests at a location to be inspected, as depicted in block 802, then sending ultrasound waves from the transducer 42 through the ultrasound gel pad (i.e., the conforming solid material 16) and the water on the inner surface 22 of the hollow composite part 20, as depicted in block 804. Then the method 800 may comprise receiving, with the transducer 42, ultrasound waves reflected off of various surfaces of or defects within the hollow composite part 20 to detect defects present within the hollow composite part 20, as depicted in block 806.

The method 800 may also comprise pivoting one portion of the support frame 12 relative to another portion of the support frame 12 to accommodate for variations in angles and cross-sections of the hollow composite part 20, as depicted in block 808. Additionally, the method may include the step of feeding water to the sponge (i.e., the pre-wetting apparatus 18) before and/or during actuation of the inspection apparatus 10 through the hollow composite part 20, as depicted in block 810. Furthermore, the method 800 may comprise comparing the ultrasound waves received with the transducer 42 with known or desired ultrasound waves to determine if the inner surface 22 has a defect, as depicted in block 812. This comparing step may be performed by a technician or may be performed by a processor, computer, or other automated means. In this example embodiment of the invention, the sponge may be located next to and ahead of the transducer 42 and ultrasound gel pad on the support frame 12 such that a path on the inner surface 22 contacted by the sponge is subsequently traveled by the ultrasound gel pad.

Although the invention has been described with reference to the preferred embodiments illustrated in the attached drawing figures, it is noted that equivalents may be employed and substitutions made herein without departing from the scope of the invention as recited in the claims.

Having thus described various embodiments of the invention, what is claimed as new and desired to be protected by Letters Patent includes the following:

1. An inspection apparatus comprising:
   a support frame;
   an inspection probe attached to the support frame and configured for sending and receiving wireless signals;
   a conforming solid material attached to an outer surface of the inspection probe, wherein the conforming solid material is configured to propagate the wireless signals from the inspection probe therethrough; and
   a pre-wetting apparatus attached to the support frame and configured to leave a trail of liquid on a surface to be inspected by the inspection probe,
   wherein the pre-wetting apparatus comprises a sponge configured to be saturated with water or another liquid for prewetting the surface to be inspected.

2. The apparatus of claim 1, wherein the support frame comprises at least two portions pivotally connected with each other to accommodate for variations in angles and cross-sections of a hollow part being inspected by the inspection apparatus.

3. The apparatus of claim 1, wherein the inspection probe comprises one or more transducers.

4. The apparatus of claim 1, further comprising a liquid delivery component configured to deliver water or another liquid to the sponge.

5. The apparatus of claim 1, wherein the conforming solid material is at least one of an ultrasound gel pad, rubber, a thermoplastic elastomer (TPE), and a styrene block copolymer.

6. The apparatus of claim 1, further comprising an actuation system configured for moving the support frame within a hollow composite part.

7. The apparatus of claim 1, further comprising a resilient member or spring joining the inspection probe with the support frame.

8. An inspection apparatus comprising:
   a support frame;
   at least one transducer having an outer surface, wherein the transducer is attached to the support frame and configured for sending and receiving ultrasound waves or vibrations;
   a conforming solid material attached to the outer surface of the transducer, wherein the conforming solid material is configured to rest between the transducer and a surface to be inspected, wherein the conforming solid material is at least one of a thermoplastic elastomer (TPE) and a styrene block copolymer; and
   a pre-wetting apparatus attached to the support frame and configured to leave a trail of liquid on the surface to be inspected, such that the liquid rests between the conforming solid material and the surface to be inspected,
   wherein the pre-wetting apparatus comprises a sponge configured to be saturated with water or another liquid for prewetting the surface to be inspected.

9. The apparatus of claim 8, wherein the support frame comprises at least two portions pivotally connected with each other to accommodate for variations in angles and cross-sections of a hollow part being inspected by the inspection apparatus.

10. The apparatus of claim 8, further comprising a resilient member or spring joining the transducer with the support frame.

11. The apparatus of claim 8, further comprising an actuation system configured for moving the support frame within a hollow composite part.

12. The apparatus of claim 8, wherein the pre-wetting apparatus comprises at least two sponges attached to the support frame, wherein at least one of the transducer and the conforming solid material is located between the two sponges.

13. A method for inspecting an inner surface of a hollow composite part, the method comprising:
   actuating an inspection apparatus through at least a portion of the hollow composite part until the inspection apparatus rests at a location to be inspected, wherein the inspection apparatus comprises:
   a support frame,
   at least one transducer having an outer surface, the transducer being attached to the support frame and configured for sending and receiving ultrasound waves,
   an ultrasound gel pad attached to the outer surface of the transducer, and
   a sponge attached to the support frame and configured to leave a trail of water on the inner surface of the hollow composite part, such that the water rests between the ultrasound gel pad and the inner surface once the inspection apparatus reaches the location to be inspected
   sending ultrasound waves from the transducer through the ultrasound gel pad and the water on the inner surface of the hollow composite part; and
   receiving, with the transducer, ultrasound waves reflected off of surfaces of the hollow composite part or reflected off of defects within the hollow composite part.

14. The method of claim 13, wherein the support frame comprises at least two portions pivotally connected with each other, wherein the method further comprises pivoting one portion of the support frame relative to another portion of the support frame to accommodate for variations in angles and cross-sections of the hollow composite part.

15. The method of claim 13, further comprising feeding water to the sponge at least one of before and during actuation of the inspection apparatus through the hollow composite part.

16. The method of claim 13, further comprising comparing the ultrasound waves received with the transducer with known or desired ultrasound waves to determine if the inner surface has a defect.

17. The method of claim 13, wherein the sponge is located next to and ahead of the transducer and ultrasound gel pad on the support frame such that a path on the inner surface contacted by the sponge is subsequently traveled by the ultrasound gel pad.

\* \* \* \* \*